United States Patent
Takamori

(10) Patent No.: US 10,438,336 B2
(45) Date of Patent: Oct. 8, 2019

(54) DRUG INSPECTION DEVICE, DRUG INSPECTION METHOD, AND PROGRAM

(71) Applicant: FUJIFILM Corporation, Tokyo (JP)

(72) Inventor: Tetsuya Takamori, Ashigarakami-gun (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 64 days.

(21) Appl. No.: 15/896,242

(22) Filed: Feb. 14, 2018

(65) Prior Publication Data

US 2018/0174292 A1 Jun. 21, 2018

Related U.S. Application Data

(63) Continuation of application No. PCT/JP2016/077675, filed on Sep. 20, 2016.

(30) Foreign Application Priority Data

Sep. 28, 2015 (JP) .................. 2015-189530

(51) Int. Cl.
*G06K 9/00* (2006.01)
*G06T 7/00* (2017.01)
(Continued)

(52) U.S. Cl.
CPC .............. *G06T 7/0004* (2013.01); *A61J 3/00* (2013.01); *G06K 9/2063* (2013.01); *G06K 9/34* (2013.01);
(Continued)

(58) Field of Classification Search
CPC ...... G06T 7/0004; G16H 20/13; G16H 20/10; G16H 30/40; G06K 9/4604; G06K 9/34;
(Continued)

(56) References Cited

U.S. PATENT DOCUMENTS

2013/0342676 A1* 12/2013 Amano ............... H04N 7/18
                                                                         348/86
2016/0104277 A1    4/2016 Takamori

FOREIGN PATENT DOCUMENTS

JP     2004-167158 A    6/2004
JP     2009-189875 A    8/2009
(Continued)

OTHER PUBLICATIONS

Communication, dated Oct. 23, 2018, issued in counterpart European Application No. 16851264.8, 10 pages in English.
(Continued)

*Primary Examiner* — Andrew M Moyer
(74) *Attorney, Agent, or Firm* — Sughrue Mion, PLLC

(57) ABSTRACT

A drug inspection device includes an image acquisition unit that acquires a plurality of captured images obtained by imaging a bundle of drug sheets bundled in a state where at least some thereof overlap each other, the image acquisition unit acquiring the captured images including at least some of respective drug sheets with respect to all the drug sheets; a drug classification specifying unit that specifies a drug classification from the captured images; an outer edge information extraction unit that extracts information of an outer edge of each of the drug sheets from the captured images; a number-of-sheets counting unit that counts the number of drug sheets based on the information; an outermost layer sheet specifying unit that specifies an outermost layer sheet present on an outermost surface portion of the bundle; and a first drug counting unit that counts the number of drugs in the outermost layer sheet.

18 Claims, 10 Drawing Sheets

(51) Int. Cl.
  *A61J 3/00* (2006.01)
  *G16H 20/10* (2018.01)
  *G16H 30/40* (2018.01)
  *G06K 9/20* (2006.01)
  *G06K 9/34* (2006.01)
  *G06K 9/46* (2006.01)
  *G16H 20/13* (2018.01)

(52) U.S. Cl.
  CPC ........... *G06K 9/344* (2013.01); *G06K 9/4604* (2013.01); *G16H 20/10* (2018.01); *G16H 20/13* (2018.01); *G16H 30/40* (2018.01); *G06K 2009/2045* (2013.01); *G06K 2209/01* (2013.01)

(58) Field of Classification Search
  CPC .. G06K 9/344; G06K 9/2063; G06K 2209/01; G06K 2009/2045; A61J 3/00
  USPC ......................................................... 382/143
  See application file for complete search history.

(56) References Cited

FOREIGN PATENT DOCUMENTS

| JP | 2010-086257 A | 4/2010 |
|---|---|---|
| JP | 2013-214170 A | 10/2013 |
| JP | 2015-002917 A | 1/2015 |
| JP | 2015-073572 A | 4/2015 |
| JP | 5763256 B1 | 8/2015 |

OTHER PUBLICATIONS

Diaz et al, "A Genetic Algorithm to Segment Range Image by Edge Detection," Industrial Electronics and Control Applications, IEEE, Nov. 30, 2005, pp. 1-7, XP010922192.

Silva et al., "Edge-based image segmentation using curvature sign maps from reflectance and range images," Proceedings 2001 International Conference on Image Processing, IEEE, vol. 1, Oct. 7, 2001, pp. 730-733, XP010564963.

Mitiche et al., "Detection of Edges Using Range Information," IEEE Transactions on Pattern Analysis and Machine Intelligence, vol. 30, No. 2, Mar. 1, 1983, pp. 174-178, XP011242650.

International Search Report dated Dec. 6, 2016 in counterpart International Application No. PCT/JP2016/077675.

Written Opinion of the International Searching Authority dated Dec. 6, 2016, in counterpart International Application No. PCT/JP2016/077675.

International Preliminary Report on Patentability dated Apr. 3, 2018, in counterpart International Application No. PCT/JP2016/077675.

* cited by examiner

DRUG INSPECTION DEVICE, DRUG INSPECTION METHOD, AND PROGRAM

CROSS-REFERENCE TO RELATED APPLICATIONS

The present application is a Continuation of PCT International Application No. PCT/JP2016/077675 filed on Sep. 20, 2016 claiming priority under 35 U.S.C § 119(a) to Japanese Patent Application No. 2015-189530 filed on Sep. 28, 2015. Each of the above applications is hereby expressly incorporated by reference, in their entirety, into the present application.

BACKGROUND OF THE INVENTION

1. Field of the Invention

The present invention relates to a drug inspection device, a drug inspection method, and a program, and particularly relates to a dispensing inspection support technique for ascertaining the classification and dosage of drugs using an image processing technique including image recognition.

2. Description of the Related Art

A dispensing inspection is performed in which drugs are dispensed in a health insurance pharmacy or the like on the basis of a prescription issued by a doctor, and then it is confirmed whether or not there are mistakes in dispensing contents such as the classification and dosage of the dispensed drugs. Here, as a packaging form of drugs, a packaging form referred to as press through package (PTP) is known in which a plastic film is molded in a dome shape so that drugs are get in, and is heat-sealed with a laminate including an aluminum foil. In a dispensing inspection for drugs on which this PTP packaging is performed, a pharmacist who performs the dispensing inspection visually confirms a drug name written on at least any one of the front and rear surfaces of the PTP, the number of PTP sheets, and the number of tablets per sheet, and collates these elements with the contents of a prescription.

In this manner, since the dispensing inspection of PTP-packaged drugs in the related art depends on pharmacists who solely perform a dispensing inspection only visually observing actual PTP-packaged drugs, there is a problem in that it cannot be said that this is enough to prevent dispensing mistakes, and that the mental strain of pharmacists concerned is too much.

In order to solve this problem, a device is proposed which supports a dispensing inspection by imaging the front and rear surfaces of PTP to extract a drug name through image recognition means, and collating prescription data (JP2009-189875A and JP2004-167158A).

SUMMARY OF THE INVENTION

However, there are the following tasks in the related art proposed in JP2009-189875A and JP2004-167158A, which does not leads to the efficiency of inspection.

[Task 1] PTP-packaged drugs are often configured to be overlapped with a plurality of drug sheets and be bundled with a rubber band or the like, and the respective drug sheets are required to be taken apart for the purpose of a dispensing inspection.

[Task 2] In a dispensing inspection support device of the related art, since the number of drugs such as the number of tablets is not able to be detected, counting using special weight measurement or manpower is required.

The present invention is contrived in view of such circumstances, and an object thereof is to provide a drug inspection device, a drug inspection method, and a program which are capable of performing an accurate drug inspection by a simple operation and with good efficiency.

In order to solve the above tasks, the following aspects of the invention are provided.

According to a first aspect, there is provided a drug inspection device comprising: an image acquisition unit that acquires a plurality of captured images obtained by imaging a bundle of drug sheets bundled in a state where at least some thereof overlap each other, the image acquisition unit acquiring the plurality of captured images including at least some of respective drug sheets with respect to all the drug sheets constituting the bundle of drug sheets; a drug classification specifying unit that specifies a drug classification from at least one of the plurality of captured images; an outer edge information extraction unit that extracts information of an outer edge of each of the drug sheets constituting the bundle of drug sheets from the plurality of captured images; a number-of-sheets counting unit that counts the number of drug sheets on the basis of the information of the outer edge of the drug sheet; an outermost layer sheet specifying unit that specifies a drug sheet piece present on an outermost surface portion of the bundle of drug sheets, as an outermost layer sheet, on the basis of the information of the outer edge of the drug sheet; and a first drug counting unit that counts the number of drugs in the outermost layer sheet.

The "drug sheet" refers to a sheet having drugs packaged in a package. A representative example of the drug sheet includes a PTP drug sheet.

At least some of images in the respective drug sheets may be included among a plurality of captured images acquired by the image acquisition unit with respect to all the drug sheets constituting the bundle of drug sheets, and it is not required that at least some of images of all the drug sheets constituting the bundle of drug sheets are included among the respective captured images acquired by the image acquisition unit.

According to the first aspect, without imaging the drug sheets included in the bundle of drug sheets apart one by one, it is possible to ascertain the drug classification, the number of drug sheets, and the number of drugs in the outermost layer sheet on the basis of a plurality of captured images obtained by imaging a plurality of drug sheets collectively in a state of a bundle. Thereby, it is possible to ascertain the classification and dosage of a drug by a simple operation and with good efficiency, and to perform an accurate drug inspection.

As a second aspect, the drug inspection device of the first aspect may be configured to further comprise: a number-of-sheet-drugs acquisition unit that acquires the number of drugs per sheet of a drug sheet which is not cut off; and a second drug counting unit that counts the total number of drugs in the bundle of drug sheets on the basis of the number of drugs per sheet acquired by the number-of-sheet-drugs acquisition unit, a counting result of the number-of-sheets counting unit, and the number of drugs in the outermost layer sheet.

According to the second aspect, it is possible to ascertain the drug classification and the total number of drugs on the basis of a plurality of captured images obtained by imaging a plurality of drug sheets collectively in a state of a bundle.

The "drug sheet which is not cut off" refers to a drug sheet on which a cutoff is not performed. A drug sheet supplied from a pharmaceutical company is configured to be a drug sheet having a specific form (that is, having a regular form) for each drug classification. This drug sheet having a regular form is a "drug sheet which is not cut off". There may be a case where the outermost layer sheet is a drug sheet which is not cut off, and a case where the outermost layer sheet is a drug sheet which is cut off (that is, fraction sheet which is a portion of a drug sheet having a regular form).

As a third aspect, in the drug inspection device of the second aspect, the number-of-sheet-drugs acquisition unit may be configured to acquire the number of drugs per sheet of a drug sheet which is not cut off and has the drug classification specified by the drug classification specifying unit, from a drug information database in which the number of drugs per sheet of a drug sheet which is not cut off is recorded for each classification of a drug.

The number of sheet drugs which is the number of drugs per sheet of a drug sheet which is not cut off is determined for each classification of a drug. It is possible to record the number of sheet drugs for each classification of a drug in a drug information database. According to the third aspect, the drug information database is referenced on the basis of the drug classification specified by the drug classification specifying unit, and thus it is possible to acquire the number of corresponding sheet drugs.

As a fourth aspect, in the drug inspection device of the second aspect, the number-of-sheet-drugs acquisition unit may be configured to acquire the number of drugs contained in one drug sheet which is not cut off, on the basis of the information of the outer edge of the drug sheet and the number of drugs in the outermost layer sheet.

It is possible to ascertain a difference in shape between the outermost layer sheet and drug sheets other than the outermost layer sheet, on the basis of the information of the outer edge extracted by the outer edge information extraction unit. It is possible to estimate the number of drugs contained in one drug sheet which is not cut off, from this ascertained difference in shape and the number of drugs in the outermost layer sheet.

As a fifth aspect, the drug inspection device of any one of the second to fourth aspects may be configured to further comprise a collation unit that collates the drug classification specified by the drug classification specifying unit and the total number of drugs obtained by the second drug counting unit with dispensing information corresponding to the bundle of drug sheets.

As a sixth aspect, the drug inspection device of the fifth aspect may be configured to further comprise a display unit that displays a collation result of the collation unit.

As a seventh aspect, in the drug inspection device of any one of the first to sixth aspects, the image acquisition unit may be configured to acquire the plurality of captured images from which stereoscopic information of the bundle of drug sheets is obtained.

By using the stereoscopic information, it is possible to accurately ascertain a positional relationship between the respective drug sheets in the bundle of drug sheets, and to count the number of drug sheets more accurately.

As an eighth aspect, in the drug inspection device of the seventh aspect, the image acquisition unit may be configured to acquire the plurality of captured images including a plurality of viewpoint images having parallax.

As a ninth aspect, in the drug inspection device of the seventh or eighth aspect, the outer edge information extraction unit may be configured to detect a mutual positional relationship between the drug sheets overlapping each other in the bundle of drug sheets on the basis of the stereoscopic information obtained from the plurality of captured images, and to extract information of an outer edge of each of the drug sheets on the basis of the mutual positional relationship between the drug sheets.

As a tenth aspect, in the drug inspection device of any one of the seventh to ninth aspects, the drug sheet may be configured to have a convex receiving chamber that receives a drug, and the first drug counting unit may be configured to acquire roughness information of the drug sheet on the basis of the stereoscopic information obtained from the plurality of captured images, and counts the number of receiving chambers as the number of drugs on the basis of the roughness information.

As an eleventh aspect, in the drug inspection device of any one of the first to tenth aspects, the image acquisition unit may be configured to acquire the plurality of captured images obtained by imaging the bundle of drug sheets from a plurality of directions.

As a twelfth aspect, in the drug inspection device of any one of the first to eleventh aspects, the image acquisition unit may be configured to acquire the plurality of captured images obtained by imaging both surfaces of the drug sheets in an overlapping direction in a state where the bundle of drug sheets bundled with an annular elastic body is spread out in a fan shape.

As a thirteenth aspect, in the drug inspection device of any one of the first to twelfth aspects, the number-of-sheets counting unit may be configured to count the number of drug sheets on the basis of an intersection of the outer edges of the drug sheets extracted by the outer edge information extraction unit.

As a fourteenth aspect, in the drug inspection device of any one of the first to thirteenth aspects, the outermost layer sheet specifying unit may be configured to specify a drug sheet of which an outer edge is extracted throughout its entire circumference among the outer edges of the respective drug sheets extracted by the outer edge information extraction unit, as the outermost layer sheet.

As a fifteenth aspect, in the drug inspection device of any one of the first to fourteenth aspects, the drug classification specifying unit may be configured to extract identification information of any one of a character string indicating a classification of a drug written on a package of the drug sheet, an identification code, and a character string printed or stamped on a packaged drug from the captured images, and to specify the drug classification on the basis of the identification information.

As a sixteenth aspect, the drug inspection device of any one of the first to fifteenth aspects may be configured to further comprise an imaging unit that images the bundle of drug sheets, and the plurality of captured images may be configured to be obtained by imaging the bundle of drug sheets through the imaging unit.

According to a seventeenth aspect, there is provided a drug inspection method comprising: an image acquisition step of acquiring a plurality of captured images obtained by imaging a bundle of drug sheets bundled in a state where at least some thereof overlap each other, and acquiring the plurality of captured images including at least some of respective drug sheets with respect to all the drug sheets constituting the bundle of drug sheets; a drug classification specifying step of specifying a drug classification from at least one of the plurality of captured images; an outer edge information extraction step of extracting information of an outer edge of each of the drug sheets constituting the bundle of drug sheets from the plurality of captured images; a number-of-sheets counting step of counting the number of drug sheets on the basis of the information of the outer edge of the drug sheet; an outermost layer sheet specifying step of specifying a drug sheet piece present on an outermost surface portion of the bundle of drug sheets, as an outermost layer sheet, on the basis of the information of the outer edge of the drug sheet; and a first drug counting step of counting the number of drugs in the outermost layer sheet.

In the seventeenth aspect, it is possible to appropriately combine the same particulars as those specified in the second to sixteenth aspects. In that case, a processing unit, a functional unit or the like which is means for taking charge of a process or a function specified in the drug inspection device can be ascertained as an element of "step" of a process or an operation corresponding thereto.

According to an eighteenth aspect, there is provided a program for causing a computer to realize: an image acquisition function of acquiring a plurality of captured images obtained by imaging a bundle of drug sheets bundled in a state where at least some thereof overlap each other, and acquiring the plurality of captured images including at least some of respective drug sheets with respect to all the drug sheets constituting the bundle of drug sheets; a drug classification specifying function of specifying a drug classification from at least one of the plurality of captured images; an outer edge information extraction function of extracting information of an outer edge of each of the drug sheets constituting the bundle of drug sheets from the plurality of captured images; a number-of-sheets counting function of counting the number of drug sheets on the basis of the information of the outer edge of the drug sheet; an outermost layer sheet specifying function of specifying a drug sheet piece present on an outermost surface portion of the bundle of drug sheets, as an outermost layer sheet, on the basis of the information of the outer edge of the drug sheet; and a first drug counting function of counting the number of drugs in the outermost layer sheet.

In the program of the eighteenth aspect, it is possible to appropriately combine the same particulars as those specified in the second to thirteenth aspects. In that case, a processing unit, a functional unit or the like which is means for taking charge of a process or a function specified in the drug inspection device can be ascertained as an element of "function" of a program for performing a process or an operation corresponding thereto.

According to the present invention, it is possible to ascertain the classification and dosage of a drug from captured images obtained by imaging a bundle of drug sheets. Thereby, it is possible to perform an accurate drug inspection by a simple operation and with good efficiency. According to the present invention, it is possible to reduce a burden of a pharmacist's drug inspection.

DESCRIPTION OF THE PREFERRED EMBODIMENTS

Hereinafter, a preferred embodiment of the present invention will be described in detail with reference to the accompanying drawings.

[Outline of Drug Prescription Work]

Figure 1:
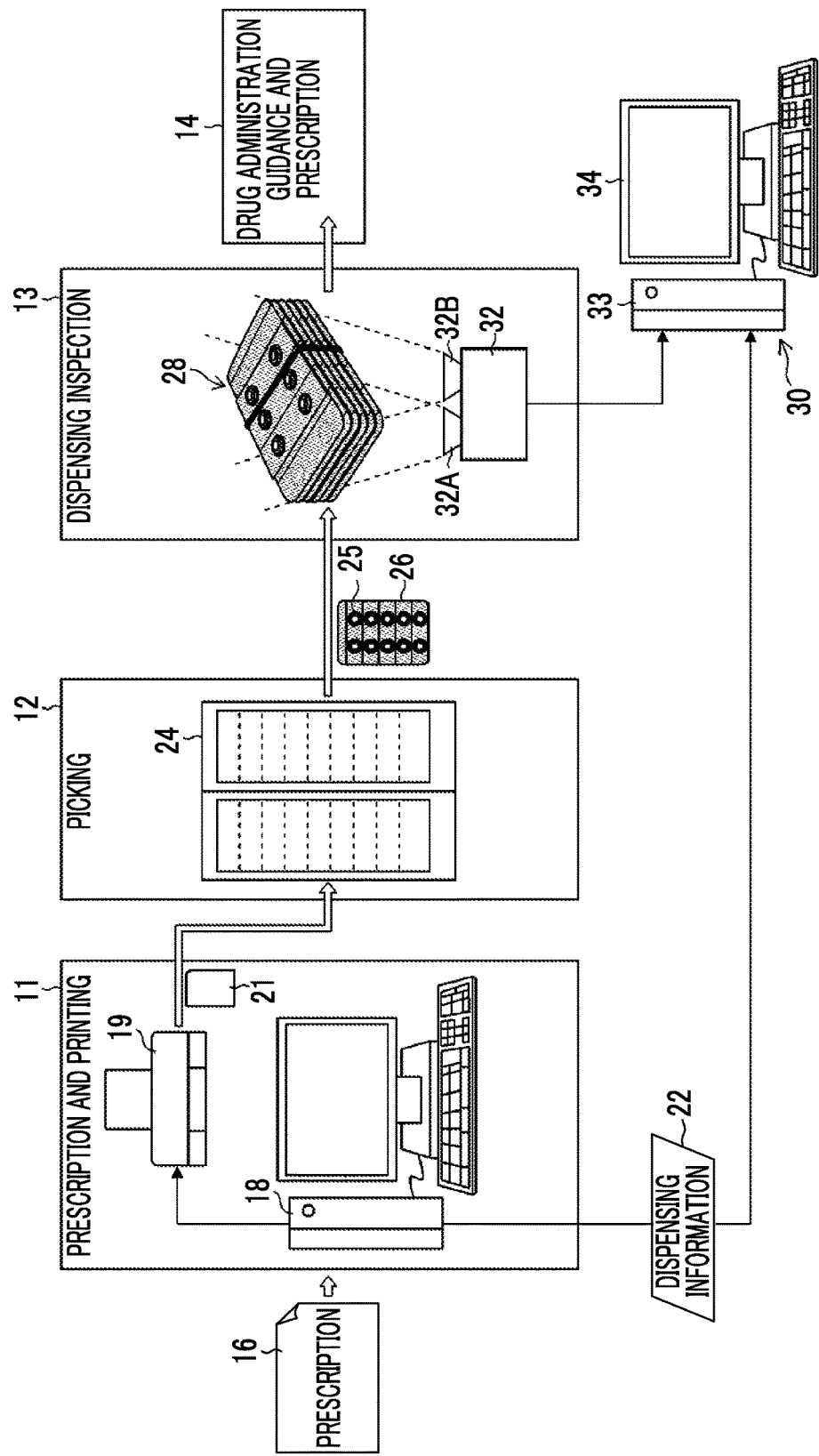
FIG. 1 is a diagram illustrating an outline of drug prescription work.

FIG. 1 is a diagram illustrating an outline of drug prescription work. Drug prescription work which is performed in a hospital, a pharmacy or the like includes prescription input and printing work 11, picking work 12, dispensing inspection work 13, and drug administration guidance and prescription work 14.

In the prescription input and printing work 11, based on dispensing information written on a prescription 16, a pharmacist inputs the dispensing information to a receipt computer 18. The dispensing information includes a patient's name and age, the classification, dosage, usage and dosage of drugs, and the like. Meanwhile, the classification of drugs input to the receipt computer 18 is not limited to drug classification written on the prescription, and may be drug classification of generic drugs having the same component and the same medical efficacy as the above classification. The drug classification is a common name specific to each drug for specifying a drug. The drug classification is synonymous with a term "drug class".

Next, a pharmacist operates the receipt computer 18, and outputs dispensing information 21 from a printer 19 connected to this receipt computer 18. In addition, the receipt computer 18 outputs dispensing information 22 to a drug inspection device 30.

In the picking work 12, a pharmacist picks drugs 25 corresponding to dispensing contents of the dispensing information 21 from a drug shelf 24, on the basis of the dispensing information 21 output from the printer 19.

The drug 25 in the present example is in tablet or capsule form, and is packaged in press through package (PTP) form. A drug sheet 26 which is a PTP drug sheet has a plurality of drugs 25 packaged therein.

In a case where a plurality of drug sheets 26 of the same drug class are picked, the plurality of drug sheets 26 are laminated together, and are bundled with a rubber band 27. The lamination is often formed in a state where the respective fronts and rears alternately overlap each other. The rubber band 27 is one form of "annular elastic body". Meanwhile, in the picking work 12, for example, an automatic picking device may be used which automatically picks drugs on the basis of the dispensing information which is input to the receipt computer 18. A bundle of drug sheets 26 picked is called a sheet bundle 28. In the present specification, the term "sheet bundle" means "a bundle of drug sheets".

In the dispensing inspection work 13, a pharmacist performs dispensing inspection for confirming whether the number of drugs 25 and the drug class thereof are correct, that is, whether they comply with the dispensing information which is input to the receipt computer 18. The drug inspection device 30 according to an embodiment of the present invention is a device that supports work of dispensing inspection performed by a pharmacist, and is used as a drug inspection support device.

In the drug administration guidance and prescription work 14, a pharmacist performs drug administration guidance for a patient after dispensing inspection, and a prescription of the drug 25.

[Configuration of Drug Inspection Device]

The drug inspection device 30 according to the embodiment of the present invention includes an imaging unit 32, an information processing device 33, and a display unit 34.

The imaging unit 32 images the sheet bundle 28 which is a subject and converts an image of the subject into an electrical signal. The imaging unit 32 of the present example has a stereoscopic imaging camera used therein which is capable of acquiring stereoscopic information of the sheet bundle 28 which is a subject. The stereoscopic imaging camera is synonymous with the terms of a compound eye camera, a stereo camera, a 3D camera, and the like. Here, 3D is an abbreviation notation of "three-dimensional" or "three dimensions".

The imaging unit 32 includes a first imaging unit 32A and a second imaging unit 32B. The same subject is imaged by each of the first imaging unit 32A and the second imaging unit 32B from different viewpoints, and thus a plurality of viewpoint images having parallax are obtained. Corresponding points are detected from a set of viewpoint images having parallax, and thus it is possible to obtain a distance from the parallax to an object.

The information processing device 33 is constituted by, for example, a personal computer. The information processing device 33 is connected to the receipt computer 18, the imaging unit 32 and the display unit 34. The "connection" is not limited to wired connection, and may be wireless connection.

The information processing device 33 determines whether the drug classification and dosage (quantity which is the number of drugs in the present example) of the drugs 25 which are targets for dispensing inspection are correct, on the basis of the dispensing information 22 acquired from the receipt computer 18 and the captured image which is image information captured by the imaging unit 32. In a case where it is not determined that the drugs 25 are correct, the information processing device 33 outputs a determination result indicating the effect to the display unit 34.

The display unit 34 displays the determination result provided from the information processing device 33.

Figure 2:
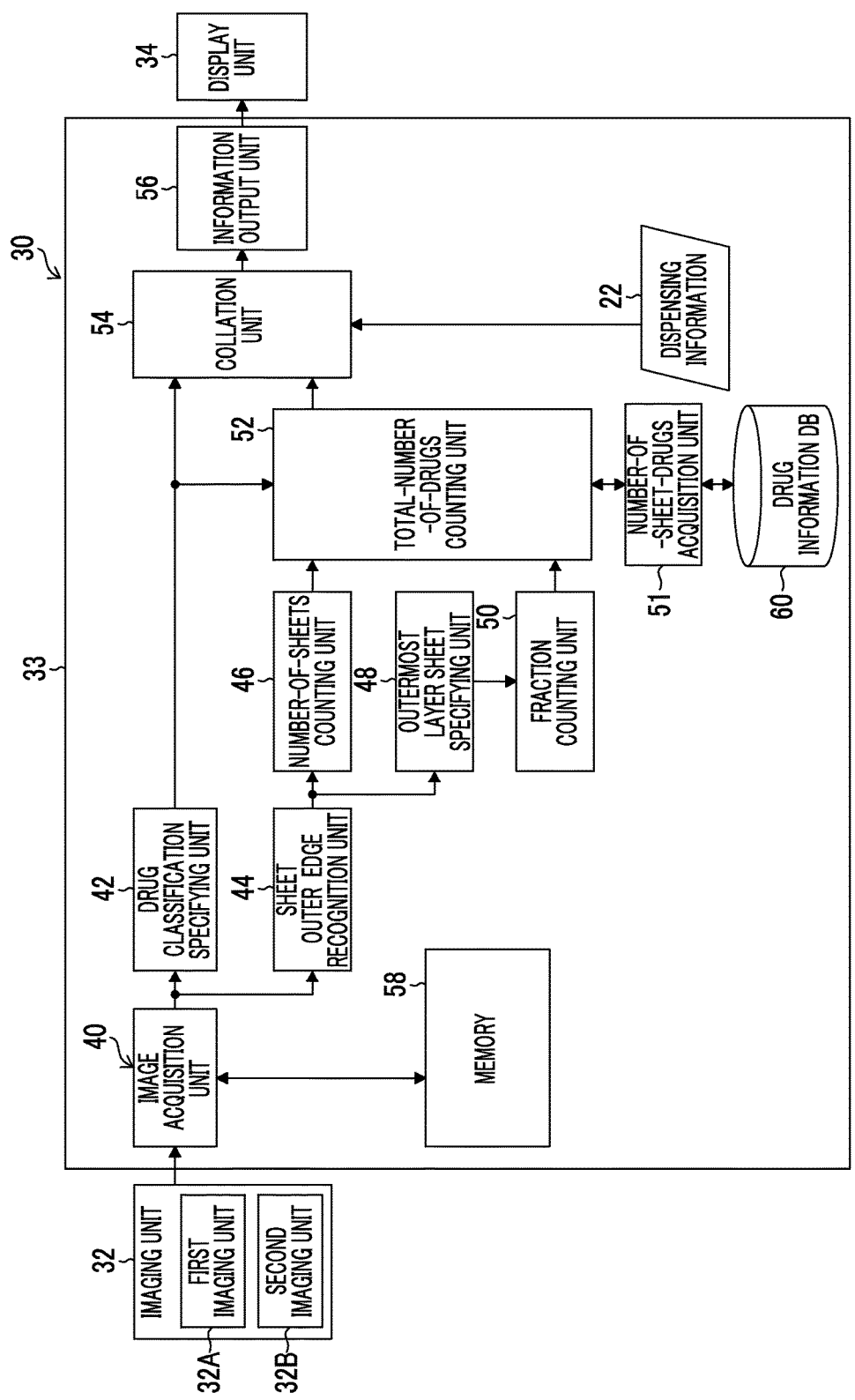
FIG. 2 is a block diagram illustrating a configuration of a drug inspection device.

FIG. 2 is a block diagram illustrating a configuration of the drug inspection device 30. In FIG. 2, components described in FIG. 1 are denoted by the same reference numerals and signs.

The imaging unit 32 converts an image of a subject into an electrical signal and generates a captured image which is image information according to the subject. In the imaging unit 32 of the present example, a captured image is obtained from each of the first imaging unit 32A and the second imaging unit 32B. The captured image is electronic image data, and the signal value of each pixel is digital image data indicated by a digital value.

The captured image captured by the imaging unit 32 is sent to the information processing device 33.

The information processing device 33 includes an image acquisition unit 40, a drug classification specifying unit 42, a sheet outer edge recognition unit 44, a number-of-sheets counting unit 46, an outermost layer sheet specifying unit 48, a fraction counting unit 50, a number-of-sheet-drugs acquisition unit 51, a total-number-of-drugs counting unit 52, a collation unit 54, and an information output unit 56. Meanwhile, the functions of these respective units are realized by a combination of hardware and software of a computer. The sheet outer edge recognition unit 44 is equivalent to one form of "outer edge information extraction unit". The fraction counting unit 50 is equivalent to one form of "first drug counting unit". The total-number-of-drugs counting unit 52 is equivalent to one form of "second drug counting unit".

The image acquisition unit 40 is means for acquiring a captured image which is captured by the imaging unit 32. The image acquisition unit 40 can be constituted by a data input terminal for fetching a captured image from the imaging unit 32. In addition, the image acquisition unit 40 may have a wired or wireless communication interface unit adopted therein. The captured image fetched from the image acquisition unit 40 is stored in a memory 58 within the information processing device 33. The memory 58 functions as an image storage unit that stores a captured image, and functions as a memory for work of the processing unit such as the drug classification specifying unit 42 or the sheet outer edge recognition unit 44.

The sheet bundle 28 is imaged by the imaging unit 32 from a plurality of directions, and a plurality of captured images are acquired. The wording "imaging from a plurality of directions" includes imaging the sheet bundle 28 from different positions by the first imaging unit 32A and the second imaging unit 32B. In addition, "imaging from a plurality of directions" includes imaging from a plurality of angles (viewpoints) by changing the posture or direction of the sheet bundle 28.

In the present embodiment, in order to ensure the acquisition of at least a portion of image information of each of the drug sheets 26 with respect to all the drug sheets 26 constituting the sheet bundle 28, the front side and the rear side are imaged in a state where the sheet bundle 28 is spread out in a fan shape. The "front side" in the sheet bundle 28 refers to a first surface side which is one surface in a lamination direction in which the drug sheets 26 overlap each other, and the "rear side" refers to a second surface side which is the other surface (surface located opposite to the first surface) in a lamination direction in which the drug sheets 26 overlap each other.

The image acquisition unit 40 acquires a plurality of captured images obtained by imaging the sheet bundle 28 bundled in a state where at least some of the drug sheets 26 overlap each other. All the drug sheets 26 constituting the sheet bundle 28 are imaged by the imaging unit 32 so that at least some of the respective drug sheets are included in a plurality of captured images acquired by the image acquisition unit 40. A function of acquiring a captured image through the image acquisition unit 40 is equivalent to one form of "captured image acquisition function".

The drug classification specifying unit 42 performs a process of specifying the classification of drugs from the plurality of captured images acquired. The drug classification specifying unit 42 specifies the drug classification by extracting character strings and/or bar codes from the entirety of some or all of the captured images among the plurality of captured images. The bar code is one form of identification code. The character string may be characters written on the package of the drug sheet 26, and may be characters printed or stamped on the drug 25.

In a case where the drug classification is specified from the character string and/or the identification code, a correspondence table which is not shown is referenced in which a correspondence relationship between the character string and/or the identification code and the drug classification is described. Data of the correspondence table between the identification code and the drug classification can be configured to be included in a drug information database 60. The processing function of the drug classification specifying unit 42 is equivalent to one form of "drug classification specifying function".

The sheet outer edge recognition unit 44 performs a process of extracting information of the outer edge of each of the drug sheets 26 in sheet bundle 28 from a plurality of captured images. In a case of the present example, it is possible to acquire stereoscopic information of the sheet bundle 28 from a plurality of captured images, and to ascertain an up-and-down relationship between the drug sheets 26 from the stereoscopic information. The term "up-and-down relationship" means an up-and-down relationship which is a positional relationship of stacking in the lamination direction of the drug sheets 26 in the sheet bundle 28. The front side in overlapping corresponds to "up", and the back side corresponds to "down".

The sheet outer edge recognition unit 44 detects a mutual positional relationship (up-and-down relationship) between the drug sheets 26 on the basis of the stereoscopic information of the sheet bundle 28 obtained from a plurality of captured images, and recognizes the outer edge of each of the drug sheets 26 on the basis of the detected positional relationship. The information of the outer edge is information indicating the boundary line of an outer circumferential edge, and is synonymous with information indicating a profile line, a boundary line, or an outer circumferential edge. The sheet outer edge recognition unit 44 is equivalent to one form of "outer edge information extraction unit". The processing function of the sheet outer edge recognition unit 44 is equivalent to one form of "outer edge information extraction function".

The number-of-sheets counting unit 46 counts the number of drug sheets 26 on the basis of the information of the outer edge of the drug sheet 26 extracted by the sheet outer edge recognition unit 44. The number-of-sheets counting unit 46 counts the number of drug sheets on the basis of the intersection of the outer edges of the respective drug sheets 26. The outer edges intersecting each other can be ascertained to be the outer edges of separate drug sheets. In addition, it is possible to ascertain whether there is a sheet completely overlapping the rear (back) of the sheet outer edge ascertained from images of the first surface and the second surface, using a difference between the forms of the front and rear of a sheet surrounded by the outer edge. Therefore, it is possible to count the number of drug sheets from an intersection relationship between the outer edges and the form of a sheet surrounded by the outer edge. The processing function of the number-of-sheets counting unit 46 is equivalent to one form of "number-of-sheets counting function".

The outermost layer sheet specifying unit 48 performs a process of specifying an outermost layer sheet which is a drug sheet piece present on the outermost surface portion located most outside in the lamination direction (synonymous with overlapping direction) of the drug sheets 26 in the sheet bundle 28, on the basis of the information of the outer edge of the drug sheet 26 obtained from the sheet outer edge recognition unit 44. The term of a drug sheet piece indicates a piece of drug sheet having the number of drugs smaller than the number of drugs of a drug sheet having a regular form by cutting off a portion of the drug sheet having a regular form, or a drug sheet having a regular form. The "drug sheet having a regular form" is a form, as it is, of a drug sheet supplied from a pharmaceutical company. In a case where the quantity of necessary drugs dispensed is a quantity except the integral multiple of the number of drugs of a drug sheet having a regular form, a drug sheet piece having the number of drugs equivalent to a fraction is disposed on the outermost surface portion of the sheet bundle 28.

The outermost layer sheet is assumed to be a fraction sheet having the number of drugs less than the number of drugs of a drug sheet having a regular form. Naturally, a case is also assumed in which the quantity of drugs dispensed is the integral multiple of the number of drugs of a drug sheet having a regular form, and the outermost layer sheet in this case is set to a drug sheet having a regular form.

The outermost layer sheet specifying unit 48 specifies an outermost layer sheet on the basis of a mutual positional relationship between the drug sheets 26 detected by the sheet outer edge recognition unit 44. In addition, the outermost layer sheet specifying unit 48 can specify a drug sheet of which the outer edge is extracted throughout its entire circumference among the outer edges of the respective drug sheets 26 extracted by the sheet outer edge recognition unit 44, as the outermost layer sheet.

The wording "the outer circumference is extracted throughout the entire circumference" means that the outer edge is not interrupted by its intersection with the outer edge of another drug sheet 26. The "entire circumference" is not limited to a case where the outer edge is a strictly closed curve, and is included in the concept of the "entire circumference", insofar as the outer edge is not interrupted by the presence of another drug sheet 26, even in a case where a portion of the outer edge is hidden by the rubber band 27, a portion of the outer edge is hidden by a pharmacist's hand having the sheet bundle 28, or the like. The outermost layer sheet specifying unit 48 recognizes a drug sheet having no intersection of the outer edge as the outermost layer sheet.

The processing function of the outermost layer sheet specifying unit 48 is equivalent to one form of "outermost layer sheet specifying function".

The fraction counting unit 50 is a processing unit that counts the number of drugs in the outermost layer sheet. The fraction counting unit 50 recognizes the number of drugs through image recognition from a captured image. The drug sheet 26 has a convex receiving chamber that receives the drug 25. The fraction counting unit 50 acquires roughness information of the outermost layer sheet on the basis of the stereoscopic information obtained from a plurality of captured images, and counts the number of convex portions of the receiving chamber on the basis of the acquired roughness information, as the number of drugs within the outermost layer sheet. The fraction counting unit 50 is equivalent to one form of "first drug counting unit". The processing function of the fraction counting unit 50 is equivalent to one form of "first drug counting function".

The number-of-sheet-drugs acquisition unit 51 performs a process of acquiring the number of drugs per sheet of a drug sheet which is not cut off. The number-of-sheet-drugs acquisition unit 51 of the present example refers to the drug information database 60 on the basis of the drug classification specified by the drug classification specifying unit 42, and obtains information of the number of drugs per sheet of a drug sheet 26 which is not cut off. The processing function of the number-of-sheet-drugs acquisition unit 51 is equivalent to one form of "number-of-sheet drugs acquisition function".

The drug information database 60 is a database in which the number of drugs per sheet of each drug sheet (which is not cut off) having a regular form is recorded for each classification of multiple kinds of drugs.

The total-number-of-drugs counting unit 52 performs a process of counting the total number of drugs of the sheet bundle 28, on the basis of the drug classification which is a specification result of the drug classification specifying unit 42, the number of sheets which is a counting result of the number-of-sheets counting unit 46, and the number of drugs in the outermost layer sheet which is a counting result of the fraction counting unit 50. The total number of drugs of the sheet bundle 28 refers to the total number of drugs included in the sheet bundle 28.

The total-number-of-drugs counting unit 52 obtains information of the number of sheet drugs (the number of drugs per sheet of a drug sheet 26 which is not cut off) acquired by the number-of-sheet-drugs acquisition unit 51.

In a method of calculating the total number of drugs in the total-number-of-drugs counting unit 52, for example, in a case where the number of drug sheets 26 excluding the outermost layer sheet in the sheet bundle 28 is set to k, the number of drugs per sheet acquired from the drug information database 60 is set to a, the number of drugs of the outermost layer sheet obtained from the fraction counting unit 50 is set to b, and the total number of drugs is set to s, the total number of drugs can be obtained according to the expression of $s=a \times k+b$. Meanwhile, k, a, and b all indicate integers equal to or greater than 1. Meanwhile, the number-of-sheets counting unit 46 may count the total number of drug sheets including the outermost layer sheet, and may count the number of drug sheets excluding the outermost layer sheet.

The total-number-of-drugs counting unit 52 is one form of "second drug counting unit". The processing function of the total-number-of-drugs counting unit 52 is equivalent to one form of "second drug counting function". The information of the total number of drugs obtained in the total-number-of-drugs counting unit 52 is sent to the collation unit 54.

The collation unit 54 performs a process of collating the drug classification specified by the drug classification specifying unit 42 and the total number of drugs obtained by the total-number-of-drugs counting unit 52 with the dispensing information 22. The dispensing information 22 is provided from the receipt computer 18 (see FIG. 1) to the information processing device 33.

The information output unit 56 is an output interface unit for outputting information of a collation result of the collation unit 54 to the outside. The information output unit 56 of the present example includes a display control circuit that performs a process of generating a signal for display on the display unit 34, and an output terminal of a signal for display on the display unit 34. The collation result of the collation unit 54 is output to the display unit 34 through the information output unit 56.

[Example of Drug Sheet]

Figure 3:
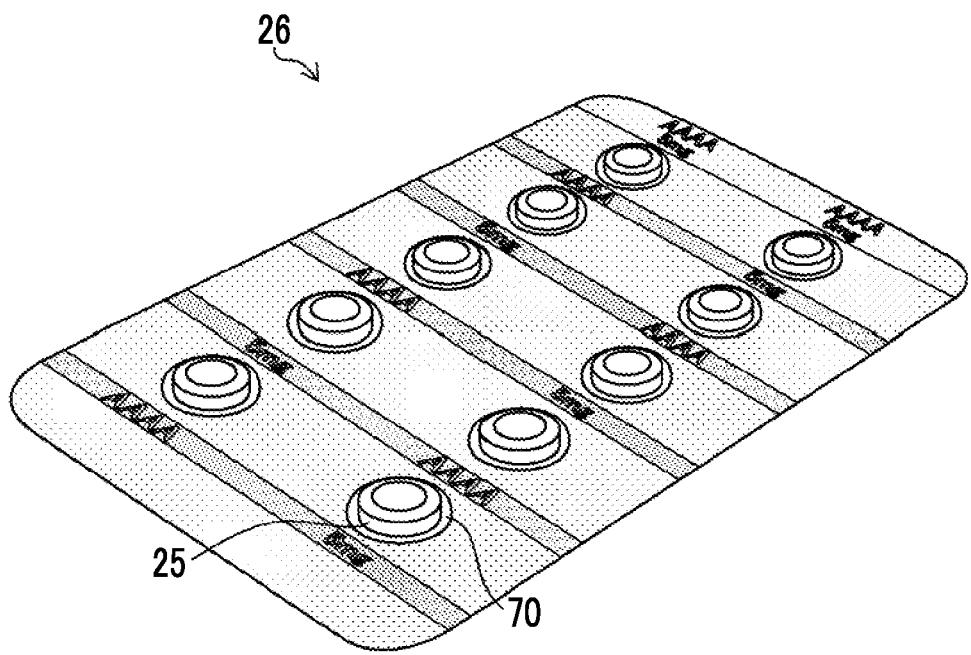
FIG. 3 is a perspective view illustrating an example of a drug sheet.

FIG. 3 is a perspective view illustrating an example of the drug sheet 26. The drug sheet 26 shown in FIG. 3 is a PTP drug sheet in which the drug 25 which is a tablet is packaged. A plurality of (ten in the example of FIG. 3) drugs 25 are packaged in one drug sheet 26. The number of drugs per sheet is not limited to ten, and may have various forms such as seven, fourteen, and twenty depending on the classification of drugs.

The drug sheet 26 has a convex receiving portion 70 in which the drug 25 is received. The receiving portion 70 is formed to be a dome-like convex portion of which the longitudinal cross section has a semicircular shape or a semi-elliptical shape, or a shape approximately similar to these shapes. The receiving portion 70 is provided only on the one-sided surface of the drug sheet 26. The one-sided surface provided with the receiving portion 70 in the drug sheet 26 is called the "front surface" of the drug sheet 26, and the surface located opposite to the receiving portion 70 is called the "rear surface" of the drug sheet 26.

Figure 4B:
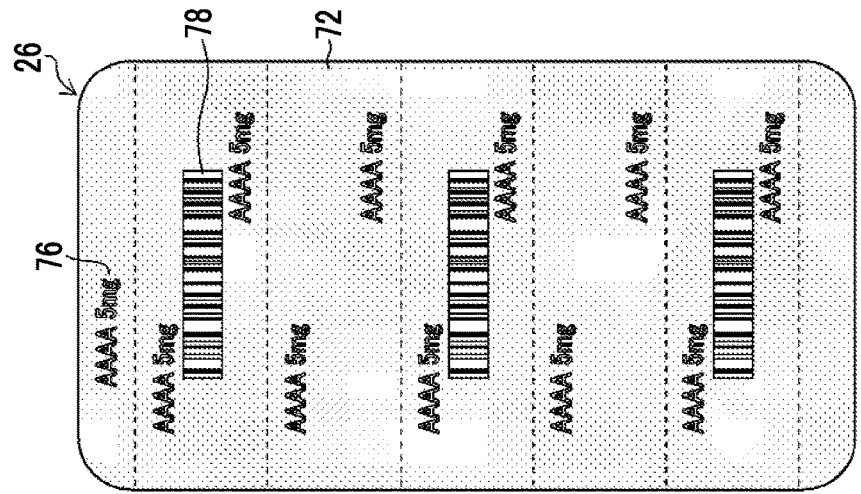
FIG. 4B is a plan view of the rear surface of the drug sheet.
Figure 4A:
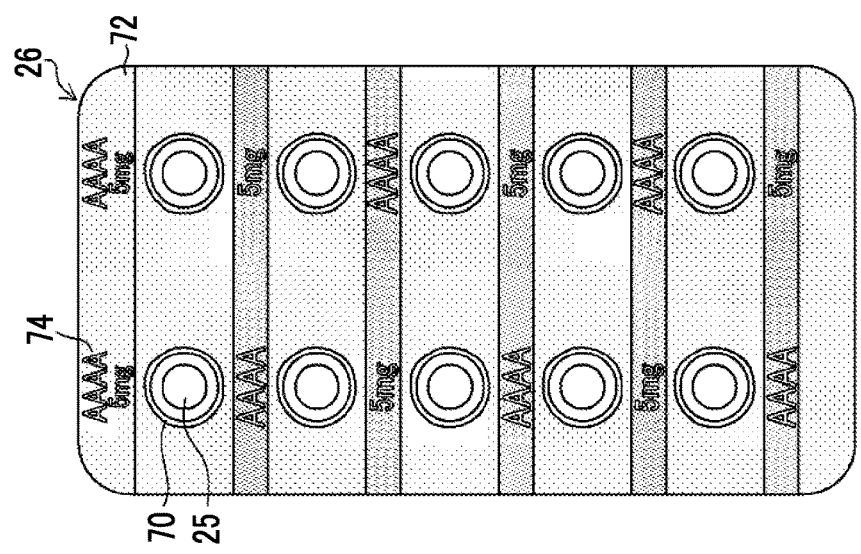
FIG. 4A is a plan view of the front surface of the drug sheet.

FIG. 4A is a plan view of the front surface of the drug sheet 26, and FIG. 4B is a plan view of the rear surface of the drug sheet 26. As shown in FIGS. 4A and 4B, character strings 74 and 76 indicating a drug classification and a bar code 78 are written on a package 72 of the drug sheet 26. Meanwhile, the disposition forms of the character strings 74 and 76 and the bar code 78 are not limited to the shown example, and may have various forms. In the example shown in FIGS. 4A and 4B, the character string 74 is written on a plurality of locations of the front surface of the drug sheet 26, and the character string 76 is written on a plurality of locations of the rear surface, but at least one of the character strings 74 and 76 may be written on at least one of the front surface and the rear surface.

In addition, the bar code 78 of the present example is written only on the rear surface of the drug sheet 26, but the bar code 78 may be written on the front surface of the drug sheet 26. In addition, the bar code 78 may be written on both the front surface and the rear surface of the drug sheet 26, depending on the drug class. In addition, the bar code 78 may not be written on the drug sheet 26, depending on the drug class.

Meanwhile, though not shown in FIGS. 4A and 4B, a character indicating the drug class may be printed or stamped on the drug 25 itself.

Figure 5:
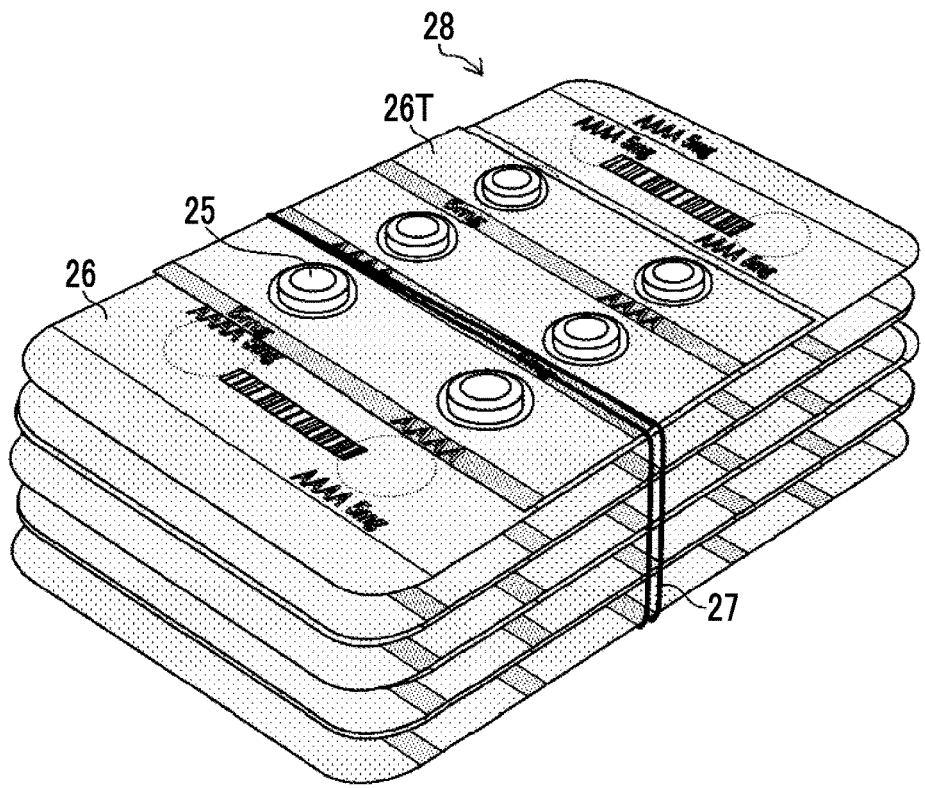
FIG. 5 is a perspective view illustrating an example of a sheet bundle obtained by bundling a plurality of drug sheets.

FIG. 5 is a perspective view illustrating an example of the sheet bundle 28 obtained by bundling a plurality of drug sheets 26. The plurality of drug sheets 26 are bundled with the rubber band 27 in a state the front surfaces or the rear surfaces are laminated facing each other. In FIG. 5, an outermost layer sheet 26T present on the outermost surface portion which is an uppermost layer is set to a fraction sheet. Meanwhile, the drug 25 may be in capsule form without being limited to the tablet form.

Figure 6:
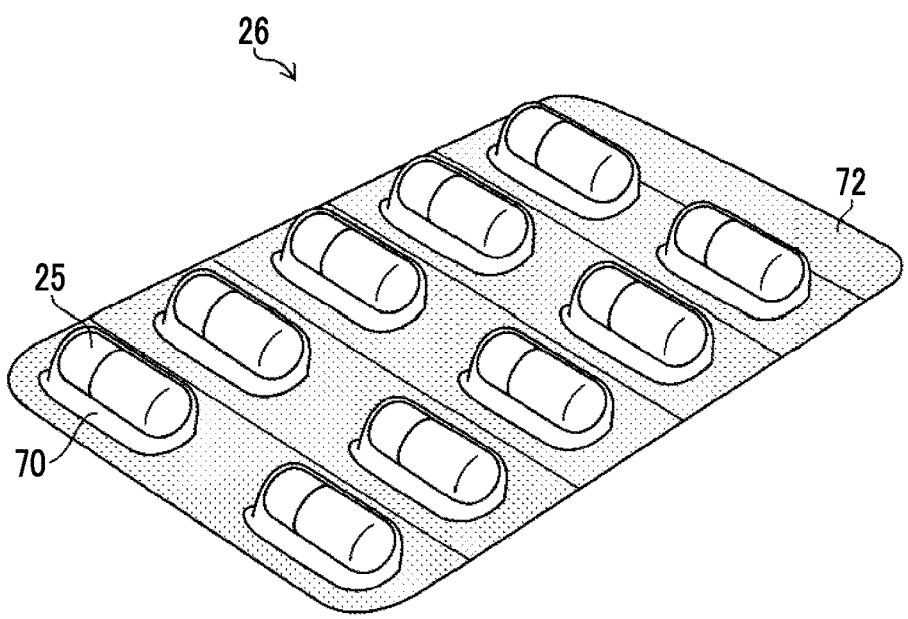
FIG. 6 is a perspective view illustrating an example of a drug sheet in capsule form.

FIG. 6 is a perspective view illustrating an example of a drug sheet in capsule form. In FIG. 6, Components which are the same as or similar to those described in FIG. 3 are denoted by the same reference numerals and signs, and thus the description thereof will not be given. In FIG. 6, for convenience of illustration, character strings and the like written on the package 72 are not written.

Figure 7:
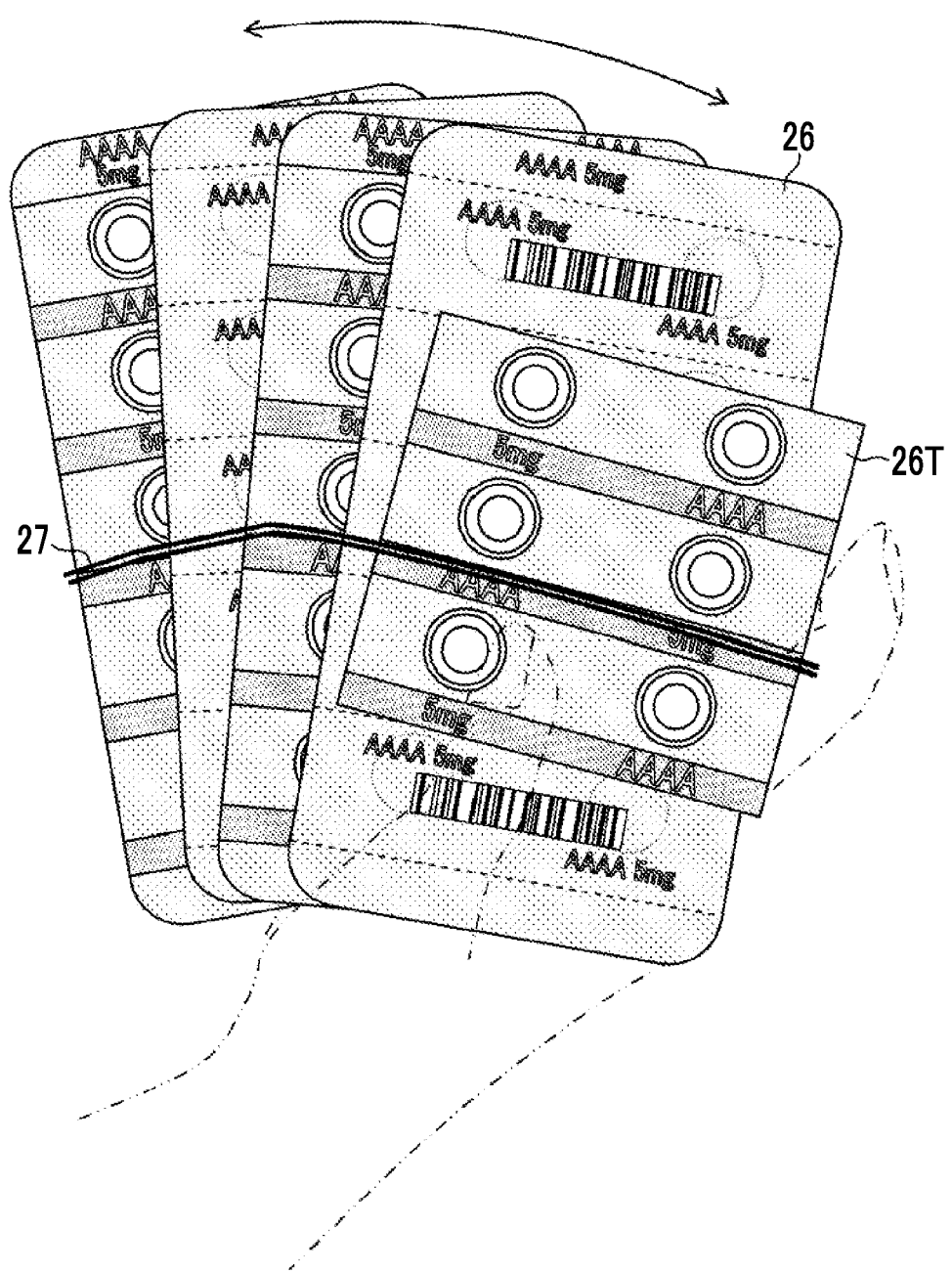
FIG. 7 is a diagram illustrating an example of a state of the sheet bundle when the sheet bundle is imaged.

FIG. 7 is a diagram illustrating an example of a state of the sheet bundle 28 when the sheet bundle 28 is imaged by the imaging unit 32. In the present example, with the sheet bundle 28 bundled with the rubber band 27, as shown in FIG. 7, both the front side and the rear side are imaged in a state where the drug sheets 26 are spread out in a fan shape. The fan shape indicates a state where a plurality of drug sheets 26 are spread in a substantially arc shape to shift the drug sheets 26 in the direction of the sheet surface, centering on the vicinity of one end in a longitudinal direction in the plurality of drug sheets 26. A pharmacist may spread out the sheet bundle 28 in a fan shape with his (or her) hand as shown in FIG. 7, and may realize a state as shown in FIG. 7 using a mechanical device which is not shown.

The drug sheets 26 are shifted bit by bit in the direction of the sheet surface and are spread as shown in FIG. 7, and thus it is easy to confirm the presence or absence of mixture of a different kind of sheet or the omission of the number of sheets.

Figure 8:
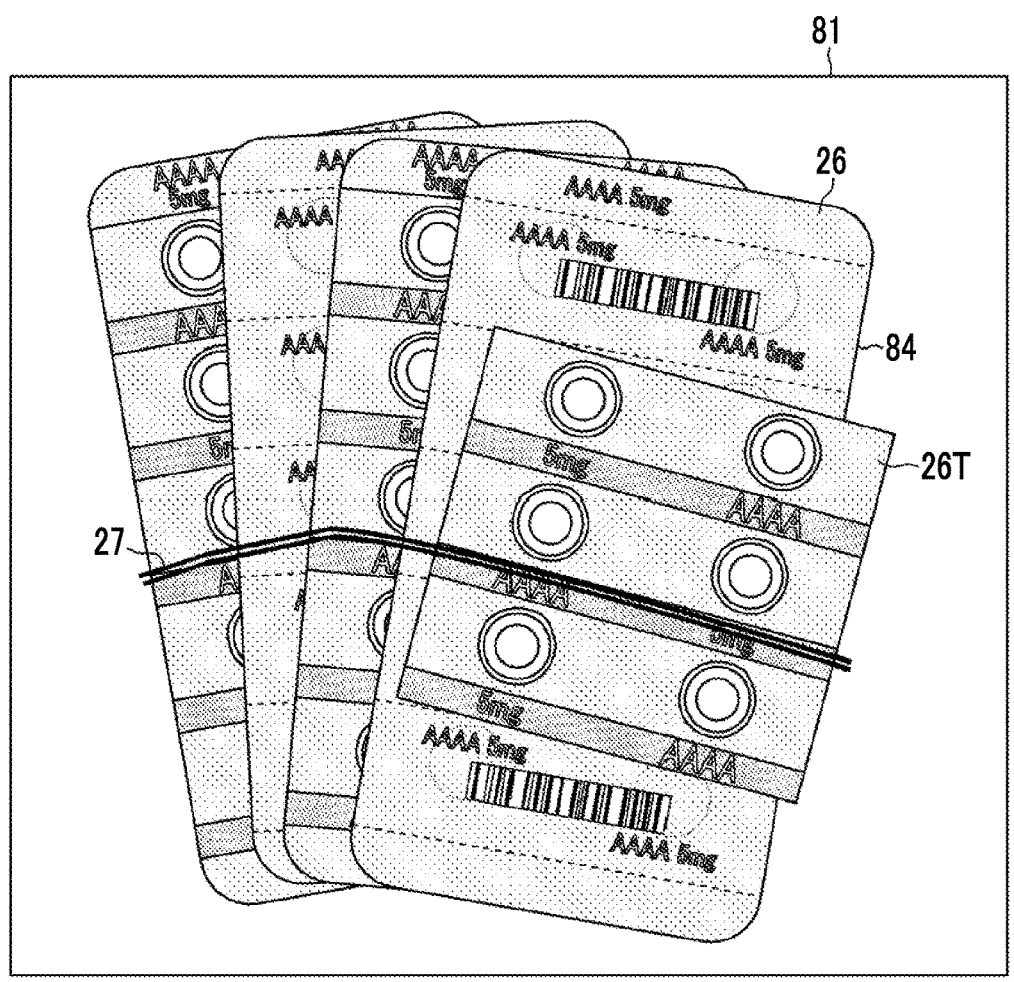
FIG. 8 is a diagram illustrating a captured image which is captured from the front side of a sheet bundle 28 of FIG. 7.
Figure 9:
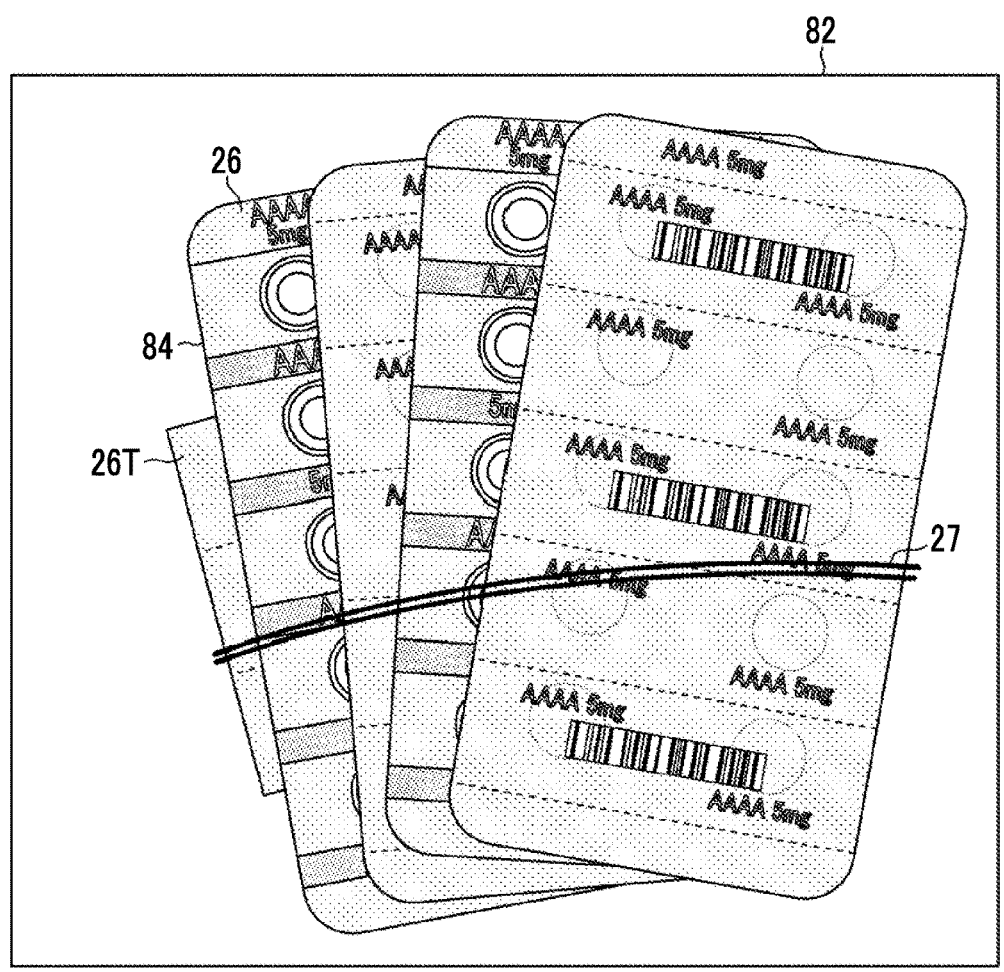
FIG. 9 is a diagram illustrating a captured image which is captured from the rear side of the sheet bundle.

FIG. 8 is an example of a captured image 81 captured from the front side of the sheet bundle 28 which is spread out in a fan shape, and FIG. 9 is an example of a captured image 82 captured from the rear side of the sheet bundle. Meanwhile, for convenience of illustration, an image element of a hand having the sheet bundle 28 is omitted. Here, a surface when seen from a side where the drug sheet (outermost layer sheet 26T) which is a fraction sheet is disposed on the uppermost layer is set to a surface on the front side. In addition, in FIGS. 8 and 9, for the purpose of the simplification of illustration, the number of drug sheets 26 is depicted with a further reduction in number than in FIG. 5.

As shown in FIGS. 8 and 9, the captured images 81 and 82 on the front side and the rear side are acquired by imaging both surfaces of the sheet bundle 28, and thus it is possible to obtain at least a portion of image information of each of all the drug sheets 26 included in the sheet bundle 28. Information of an outer edge 84 of each of the drug sheets 26 is extracted from such captured images 81 and 82, and the number of drug sheets 26 is ascertained on the basis of the outer edge information.

[Procedure of Drug Inspection Method]

Figure 10:
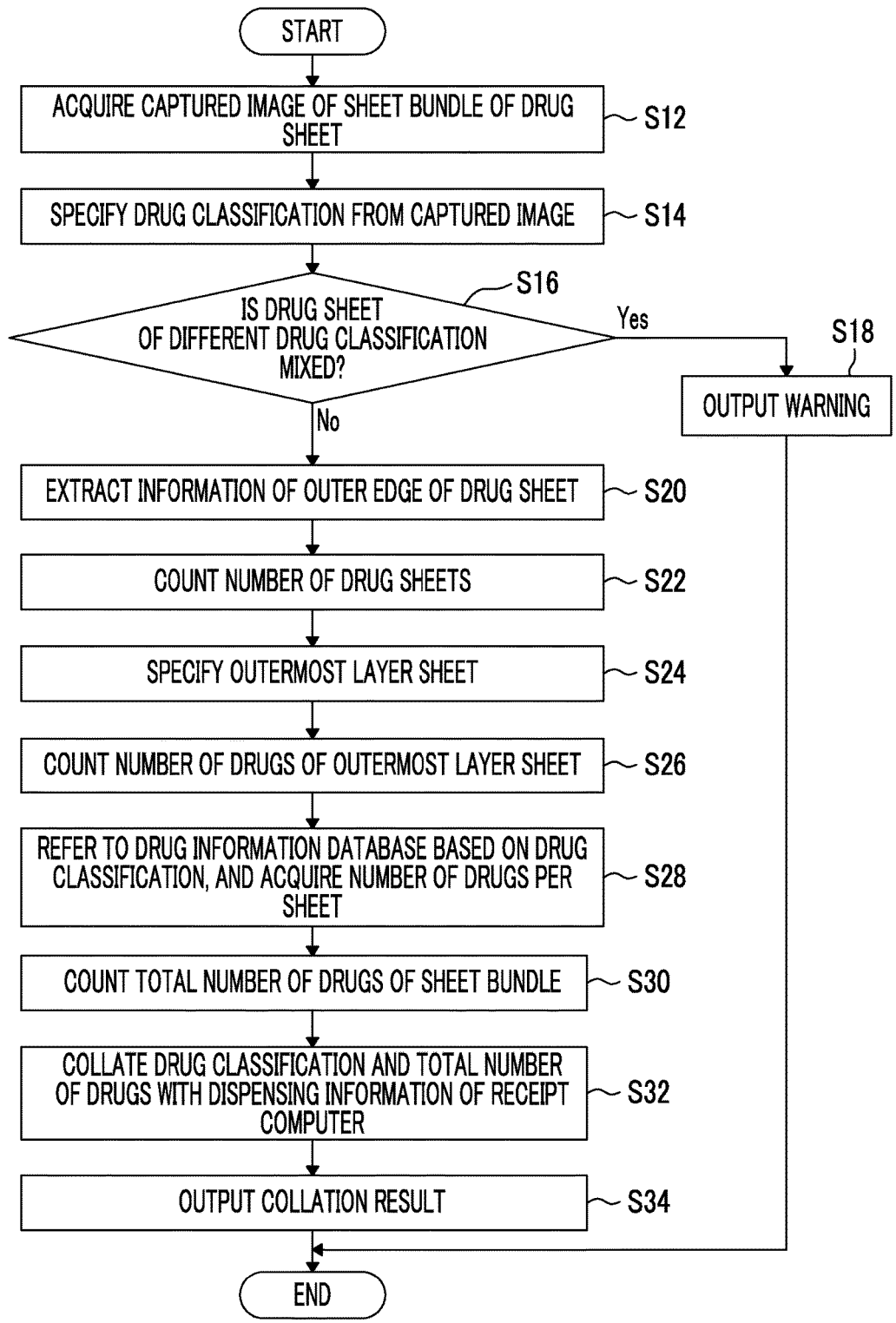
FIG. 10 is a flow diagram illustrating a procedure of a drug inspection method in the present embodiment.

FIG. 10 is a flow diagram illustrating a procedure of a drug inspection method using the drug inspection device 30. The drug inspection method can be used as a dispensing inspection support method. The flow diagram of FIG. 10 shows a procedure of processes in the drug inspection device 30.

First, a captured image of the sheet bundle 28 of the drug sheets 26 is acquired (step S12). In step S12, as described in FIGS. 7 to 9, a plurality of captured images are acquired which are obtained by imaging all the drug sheets 26 constituting the sheet bundle 28 so that at least some of the respective drug sheets 26 are included. Step S12 is equivalent to one form of "image acquisition step".

Next, the drug classification is specified from the captured images (step S14). In step S14, the character strings 74 and 76 and/or the bar code 78 is recognized from at least one of the plurality of captured images acquired in step S12 and a process of specifying the drug classification is performed. The process of step S14 is performed by the drug classification specifying unit 42 of FIG. 2. Step S14 is equivalent to one form of "drug classification specifying step".

In a case where a drug sheet 26 of a different drug class is mixed in the sheet bundle 28, it is also assumed that a plurality of drug classifications are detected in step S14. The presence or absence of mixture of a different kind of sheet is expected to be visually confirmed by a pharmacist. However, in the drug inspection device 30 of the present embodiment, in a case where a plurality of drug classifications are detected from the captured images, it is determined that a different kind of sheet is mixed and a warning for giving notice of the effect is output.

That is, a determination is made of whether a drug sheet 26 of a different drug classification is mixed in step S16, and in a case where it is determined that a different kind of sheet is mixed, a warning of the effect is output (step S18). In a method of outputting a warning, in addition to warning display on the display unit 34, notice through a voice may be performed in combination with the warning display.

In a case where it is determined in step S16 that a drug sheet of a different drug classification is not mixed, the flow proceeds to step S20. In step S20, information of the outer edge 84 of the drug sheet 26 is extracted from the captured images. The process of step S20 is performed by the sheet outer edge recognition unit 44 of FIG. 2. Step S20 is equivalent to one form of "outer edge information extraction step".

Next, the number of drug sheets 26 is counted on the basis of the information of the outer edge 84 of the drug sheet 26 (step S22). The process of step S22 is performed by the number-of-sheets counting unit 46 of FIG. 2. Step S22 is equivalent to one form of "number-of-sheets counting step".

In addition, the outermost layer sheet 26T is specified on the basis of the information of the outer edge of the drug sheet 26 (step S24). The process of step S24 is performed by the outermost layer sheet specifying unit 48 of FIG. 2. Step S24 is equivalent to one form of "outermost layer sheet specifying step". Meanwhile, the order of processes of step S22 and step S24 can be switched.

Next, the number of drugs of the outermost layer sheet 26T is counted (step S26). The process of step S26 is performed by the fraction counting unit 50 of FIG. 2. The process of step S26 is equivalent to one form of "first drug counting step".

On the other hand, the drug information database 60 is referenced on the basis of the drug classification specified in step S14, and the number of drugs per sheet in a drug sheet 26 having a regular form according to the specified drug classification is acquired (step S28). The process of step S28 is equivalent to one form of "number-of-sheet drugs acquisition step". The total number of drugs of the sheet bundle 28 is counted on the basis of the number of drugs per sheet acquired in step S28, the number of drug sheets 26 ascertained in step S22, and the number of drugs of the outermost layer sheet 26T ascertained in step S22 (step S30). The processes of step S28 and step S30 are performed by the total-number-of-drugs counting unit 52 of FIG. 2. Step S30 is equivalent to one form of "second drug counting step". Meanwhile, the processing order of step S28 is not limited to immediately before step S30, and can be performed at an appropriate timing from step S14 and the subsequent steps to a step before step S30.

Next, the drug classification specified in step S14 and the total number of drugs obtained in step S30 are collated with the dispensing information 22 of the receipt computer 18 (step S32). The process of step S32 is performed by the collation unit 54 of FIG. 2.

A collation result of step S32 is output (step S34). The process of step S34 is performed through the information output unit 56 of FIG. 56. When the collation result is output, only in a case of not being coincident with the dispensing information 22, such as the excess or deficiency of the number of drugs, information for giving notice of the non-coincidence may be output, and even in a case of being coincident with the dispensing information 22, information for giving notice of the coincidence may be output. A user's (such as a pharmacist) attention relating to a mistake of dispensing can be attracted by the output of the collation result in step S34 or the warning output in step S18.

[With Respect to Various Forms of Drug Inspection Device]

Modification Example 1

The drug inspection device 30 is not limited to a form which is realized by a computer system described in FIG. 1, and can be configured as a form which is realized by a wearable terminal based on a spectacle type (goggle type)

head mounted display system. According to such a form, dispensing inspection support based on augmented reality (AR) can be performed.

Modification Example 2

In FIG. 2, a form in which the information processing device 33 includes the drug information database 60 is shown, but the drug information database 60 may be installed outside of the information processing device 33. For example, the drug information database 60 may be held in the receipt computer 18. In addition, the drug information database 60 may be held in another computer which is not shown, and can also have a form in which the information processing device 33 acquires information from the drug information database 60 through a network. As an "external device" holding the drug information database 60, for example, a server connected to a network which is not shown can be used. The network can be a local area network or a wide area network, or be configured in combination thereof.

Modification Example 3

An example has been described in which the number-of-sheet-drugs acquisition unit 51 described in FIG. 2 acquires the number of sheet drugs from the drug information database 60, but is not limited to such a form. As another form, the number-of-sheet-drugs acquisition unit 51 may acquire the number of drugs contained in one drug sheet which is not cut off, on the basis of the information of the outer edge of the drug sheet obtained from the sheet outer edge recognition unit 44 and the number of drugs in the outermost layer sheet obtained from the fraction counting unit 50. For example, the number-of-sheet-drugs acquisition unit 51 can be configured to acquire the number of sheet drugs by ascertaining a difference in shape between the outermost layer sheet 26T and the drug sheets 26 (drug sheets which are not cut off) other than that, from the information of the outer edge of each drug sheet obtained from the sheet outer edge recognition unit 44, and performing an arithmetic operation for estimating the number of drugs contained in one drug sheet which is not cut off, from a ratio between the sheet areas of the outermost layer sheet 26T and the drug sheets 26 other than that and the number of drugs on the outermost layer sheet 26T.

Modification Example 4

As means for acquiring stereoscopic information, for example, the following means can also be adopted without being limited to a form in which the stereoscopic imaging camera exemplified above is used.

That is, an object which is a subject is irradiated with linear illumination light in an oblique direction, and its reflected light is captured by a camera. In a case where roughness is present on the object, a position on which the linear illumination light falls changes depending on the height of the convex portion. Therefore, the object is scanned by moving a position at which the object is irradiated with the linear illumination light, and its reflected light is imaged by a camera directly facing the object, whereby a reflection image obtained by reflecting the shape of the convex portion (bulged portion) is obtained. The image captured in this manner is also one form of "captured image", and the number of drug sheets 26 or the outermost layer sheet can be recognized on the basis of "a plurality of captured images" including such a captured image.

Modification Example 5

As another means for acquiring stereoscopic information, a form can also be configured in which distance image acquisition based on a time of flight (TOF) type is used. In the TOF type, an object is irradiated with infrared light, and reflected light from the object is received, whereby information of distance to each position on the object can be acquired on the basis of the phase of the received reflected light. The obtainment of image information corresponding to distance to each position of the object by a TOF type camera is included in the concept of "imaging". The TOF type camera is one form of "imaging unit", and the image information obtained by the TOF type camera is one form of "captured image".

Modification Example 6

It is preferable that the imaging unit 32 has means capable of acquiring stereoscopic information adopted therein, but the imaging unit is not necessarily limited to a unit capable of acquiring stereoscopic information. Even in a case of a planar image, a positional relationship between drug sheets in an overlapping direction can be ascertained from an intersection relationship between the outer edges. By using this, it is possible to ascertain the number of drug sheets from the captured image, and to specify the outermost layer sheet.

Modification Example 7

The imaging unit 32 is not limited to the generation of data of a still image, and may generate data of a motion picture. A technique for extracting the data of a still image from the data of a motion picture is well-known, and image information obtained from the data of a motion picture also corresponds to one form of "captured image".

Modification Example 8

In the above-described embodiment, an example has been described in which both the front side and the rear surface side of the sheet bundle 28 are imaged by one imaging unit 32 in two-time imaging. However, without being limited to such a form at the time of carrying out the invention, a form can also be configured in which an imaging unit that images the front side of the sheet bundle 28 and an imaging unit that images the rear side of the sheet bundle 28 are provided separately, and both sides are simultaneously imaged, to acquire each captured image.

Modification Example 9

In FIG. 7, an example has been described in which the sheet bundle 28 is imaged in a state of being spread out in a fan shape, but the state of the sheet bundle during imaging is not limited to the example described in FIG. 7. At the time of carrying out the invention, the respective drug sheets of the sheet bundle are not imaged apart one by one, and it is required that imaging is performed in a state of the sheet bundle, identification information of any one of a character string written on the package of the drug sheet, an identification code, and a character string printed or stamped on a drug can be extracted from the captured image, and at least some of the respective drug sheets with respect to all the drug sheets are imaged in order to correctly count the total number of drug sheets included in the sheet bundle. The specific state of the sheet bundle during imaging can be appropriately changed in a range satisfying such conditions.

Figure 11:
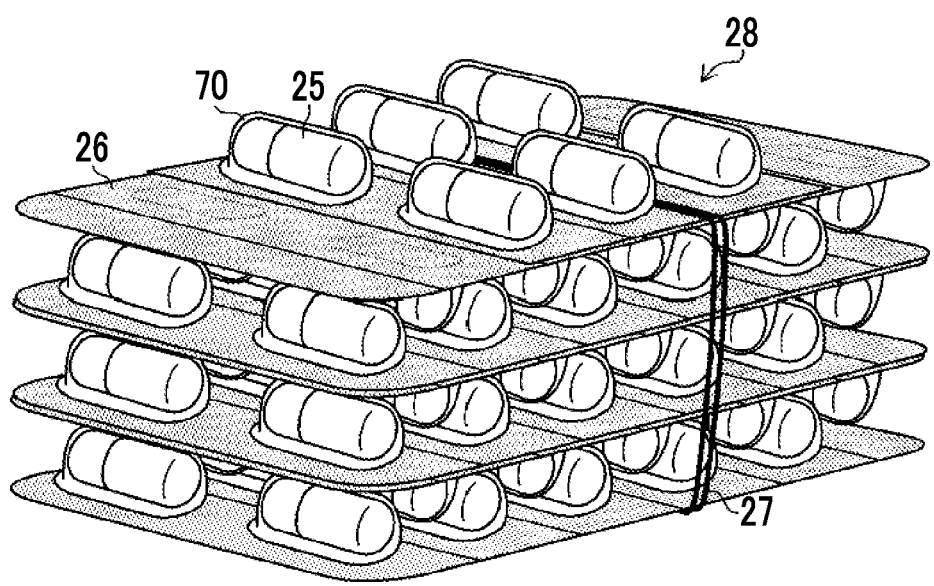
FIG. 11 is a perspective view illustrating another example of the sheet bundle.

For example, in a case where the sheet bundle 28 is imaged from a viewpoint as shown in the perspective view of FIG. 11, at least some of all the drug sheets 26 may be able to be imaged without spreading out the sheet bundle 28. At the time of carrying out the invention, imaging in a state of spreading out the sheet bundle is not necessarily required. However, for the purpose of more accurate inspection, it is preferable that a plurality of captured images are acquired by changing an imaging direction, and it is preferable that, particularly, as shown in FIG. 7, imaging is performed in a state of shifting the overlapping position of the drug sheets 26.

Meanwhile, FIG. 7 shows a state where all the drug sheets 26 in the sheet bundle 28 are spread out by mutually shifting bit by bit in the direction of the sheet surface, but some drug sheets 26 may completely overlap each other. For example, the outermost layer sheet 26T may completely overlap a second sheet. Even in such a case, both the front side and the rear side are imaged to acquire each captured image, and thus image information of each drug sheet can be obtained with respect to all the drug sheets constituting the sheet bundle 28.

Modification Example 10

In the above-described embodiment, an example has been described in which the total number of drugs in the sheet bundle 28 is counted and is collated with the dispensing information 22, but the form of the drug inspection device is not limited to this example. As the drug inspection device of another form, a device can also be used which provide information the number of drugs of the outermost layer sheet counted by the fraction counting unit 50 and information of the number of drug sheets counted by the number-of-sheets counting unit 46. Whether dosage is right or wrong can be determined on the basis of the information of the number of drugs of the outermost layer sheet and the information of the number of sheets.

Modification Example 11

In the above-described embodiment, the system configuration of the drug inspection device 30 including the imaging unit 32, the information processing device 33, and the display unit 34 has been described, but the portion of the information processing device 33 can be ascertained as one form of "drug inspection device" of the present invention, regardless of the presence or absence of provision with the imaging unit 32 and the display unit 34. In addition, the processing function of the information processing device 33 is not limited to a form realized by one computer, and a form can also be used in which the processing function is shared by a plurality of computers, and the processing function of the information processing device 33 is realized by a combination of a plurality of computers.

<With Respect to Program Causing Computer to Function as Drug Inspection Device>

A program for causing a computer to realize drug inspection functions of the information processing device 33 described in the above-described embodiment is recorded on a compact disc read-only memory (CD-ROM), a magnetic disc, and another computer readable medium (non-transitory information storage medium which is tangible), thereby allowing the program to be provided through the information storage medium. Instead of an aspect in which a program is provided in a state where the program is stored on such an information storage medium, a program signal can also be provided as a download service using a communication network such as the Internet.

In addition, some or all of the drug inspection functions described in the above-described embodiment are realized by an application server or cloud computing, and thus a service for providing processing functions through a network can also be performed.

Advantages of Embodiment

According to the embodiment of the present invention described above, there are the following advantages.

(1) The classification and dosage of a drug can be ascertained on the basis of a captured image obtained by collectively imaging the sheet bundle 28 bundled with the rubber band 27. Therefore, an inspection can be performed by a simple operation without removing the rubber band 27 of the sheet bundle 28, and without performing complicated work in which the respective drug sheets 26 are taken apart one by one and are individually imaged.

(2) The number of all drugs (the total number of drugs) included in the sheet bundle 28 can be accurately ascertained from a state where a plurality of drug sheets 26 overlap each other.

(3) It is possible to confirm consistency with the dispensing information 22 with respect to not only the drug classification but also the dosage (quantity), and to perform a drug inspection with better efficiency.

In the embodiment of the present invention described above, components can be appropriately changes, added, and deleted without departing from the spirit and scope of the present invention. The present invention is not limited to the embodiment described above, and can be variously changed and modified by those of ordinarily skilled in the art within the technical idea of the present invention.

EXPLANATION OF REFERENCES

18: receipt computer
22: dispensing information
25: drug
26: drug sheet
26T: outermost layer sheet
27: rubber band
28: sheet bundle
30: drug inspection device
32: imaging unit
32A: first imaging unit
32B: second imaging unit
33: information processing device
34: display unit
40: image acquisition unit
42: drug classification specifying unit
44: sheet outer edge recognition unit
46: number-of-sheets counting unit
48: outermost layer sheet specifying unit
50: fraction counting unit
51: number-of-sheet-drugs acquisition unit
52: total-number-of-drugs counting unit
54: collation unit
56: information output unit
60: drug information database 70: receiving portion
72: package
74, 76: character string
78: bar code
81, 82: captured image
84: outer edge

What is claimed is:

1. A drug inspection device comprising:
an image acquisition unit that acquires a plurality of captured images obtained by imaging a bundle of drug sheets bundled in a state where at least some thereof overlap each other, the image acquisition unit acquiring the plurality of captured images including at least some of respective drug sheets with respect to all the drug sheets constituting the bundle of drug sheets;
a drug classification specifying unit that specifies a drug classification from at least one of the plurality of captured images;
an outer edge information extraction unit that extracts information of an outer edge of each of the drug sheets constituting the bundle of drug sheets from the plurality of captured images;
a number-of-sheets counting unit that counts the number of drug sheets on the basis of the information of the outer edge of the drug sheet;
an outermost layer sheet specifying unit that specifies a drug sheet piece present on an outermost surface portion of the bundle of drug sheets, as an outermost layer sheet, on the basis of the information of the outer edge of the drug sheet; and
a first drug counting unit that counts the number of drugs in the outermost layer sheet.

2. The drug inspection device according to claim 1, further comprising:
a number-of-sheet-drugs acquisition unit that acquires the number of drugs per sheet of a drug sheet which is not cut off; and
a second drug counting unit that counts the total number of drugs in the bundle of drug sheets on the basis of the number of drugs per sheet acquired by the number-of-sheet-drugs acquisition unit, a counting result of the number-of-sheets counting unit, and the number of drugs in the outermost layer sheet.

3. The drug inspection device according to claim 2, wherein the number-of-sheet-drugs acquisition unit acquires the number of drugs per sheet of a drug sheet which is not cut off and has the drug classification specified by the drug classification specifying unit, from a drug information database in which the number of drugs per sheet of a drug sheet which is not cut off is recorded for each classification of a drug.

4. The drug inspection device according to claim 2, wherein the number-of-sheet-drugs acquisition unit acquires the number of drugs contained in one drug sheet which is not cut off, on the basis of the information of the outer edge of the drug sheet and the number of drugs in the outermost layer sheet.

5. The drug inspection device according to claim 2, further comprising a collation unit that collates the drug classification specified by the drug classification specifying unit and the total number of drugs obtained by the second drug counting unit with dispensing information corresponding to the bundle of drug sheets.

6. The drug inspection device according to claim 5, further comprising a display unit that displays a collation result of the collation unit.

7. The drug inspection device according to claim 1, wherein the image acquisition unit acquires the plurality of captured images from which stereoscopic information of the bundle of drug sheets is obtained.

8. The drug inspection device according to claim 7, wherein the image acquisition unit acquires the plurality of captured images including a plurality of viewpoint images having parallax.

9. The drug inspection device according to claim 7, wherein the outer edge information extraction unit detects a mutual positional relationship between the drug sheets overlapping each other in the bundle of drug sheets on the basis of the stereoscopic information obtained from the plurality of captured images, and extracts information of an outer edge of each of the drug sheets on the basis of the mutual positional relationship between the drug sheets.

10. The drug inspection device according to claim 7, wherein the drug sheet has a convex receiving chamber that receives a drug, and
the first drug counting unit acquires roughness information of the drug sheet on the basis of the stereoscopic information obtained from the plurality of captured images, and counts the number of receiving chambers as the number of drugs on the basis of the roughness information.

11. The drug inspection device according to claim 1, wherein the image acquisition unit acquires the plurality of captured images obtained by imaging the bundle of drug sheets from a plurality of directions.

12. The drug inspection device according to claim 1, wherein the image acquisition unit acquires the plurality of captured images obtained by imaging both surfaces of the drug sheets in an overlapping direction in a state where the bundle of drug sheets bundled with an annular elastic body is spread out in a fan shape.

13. The drug inspection device according to claim 1, wherein the number-of-sheets counting unit counts the number of drug sheets on the basis of an intersection of the outer edges of the drug sheets extracted by the outer edge information extraction unit.

14. The drug inspection device according to claim 1, wherein the outermost layer sheet specifying unit specifies a drug sheet of which an outer edge is extracted throughout its entire circumference among the outer edges of the respective drug sheets extracted by the outer edge information extraction unit, as the outermost layer sheet.

15. The drug inspection device according to claim 1, wherein the drug classification specifying unit extracts identification information of any one of a character string indicating a classification of a drug written on a package of the drug sheet, an identification code, and a character string printed or stamped on a packaged drug from the captured images, and specifies the drug classification on the basis of the identification information.

16. The drug inspection device according to claim 1, further comprising an imaging unit that images the bundle of drug sheets,
wherein the plurality of captured images are obtained by imaging the bundle of drug sheets through the imaging unit.

17. A drug inspection method comprising:
an image acquisition step of acquiring a plurality of captured images obtained by imaging a bundle of drug sheets bundled in a state where at least some thereof overlap each other, and acquiring the plurality of captured images including at least some of respective drug sheets with respect to all the drug sheets constituting the bundle of drug sheets;

a drug classification specifying step of specifying a drug classification from at least one of the plurality of captured images;

an outer edge information extraction step of extracting information of an outer edge of each of the drug sheets constituting the bundle of drug sheets from the plurality of captured images;

a number-of-sheets counting step of counting the number of drug sheets on the basis of the information of the outer edge of the drug sheet;

an outermost layer sheet specifying step of specifying a drug sheet piece present on an outermost surface portion of the bundle of drug sheets, as an outermost layer sheet, on the basis of the information of the outer edge of the drug sheet; and a first drug counting step of counting the number of drugs in the outermost layer sheet.

18. A non-transitory computer-readable recording medium including instructions stored thereon, such that when the instructions are read and executed by a computer, the computer is configured to realize:

an image acquisition function of acquiring a plurality of captured images obtained by imaging a bundle of drug sheets bundled in a state where at least some thereof overlap each other, and acquiring the plurality of captured images including at least some of respective drug sheets with respect to all the drug sheets constituting the bundle of drug sheets;

a drug classification specifying function of specifying a drug classification from at least one of the plurality of captured images;

an outer edge information extraction function of extracting information of an outer edge of each of the drug sheets constituting the bundle of drug sheets from the plurality of captured images;

a number-of-sheets counting function of counting the number of drug sheets on the basis of the information of the outer edge of the drug sheet;

an outermost layer sheet specifying function of specifying a drug sheet piece present on an outermost surface portion of the bundle of drug sheets, as an outermost layer sheet, on the basis of the information of the outer edge of the drug sheet; and a first drug counting function of counting the number of drugs in the outermost layer sheet.

* * * * *